(12) United States Patent
Liao

(10) Patent No.: US 7,360,402 B2
(45) Date of Patent: Apr. 22, 2008

(54) WATER QUALITY DETECTING DEVICE FOR AN AQUARIUM

(76) Inventor: Shih-Hui Liao, 6F, No. 8-5, Lane 128, Sec. 1, Nan Chu Road, Luchu Hsiang, Taoyuan County (TW)

( * ) Notice: Subject to any disclaimer, the term of this patent is extended or adjusted under 35 U.S.C. 154(b) by 286 days.

(21) Appl. No.: 11/207,667

(22) Filed: Aug. 19, 2005

(65) Prior Publication Data

US 2007/0039379 A1   Feb. 22, 2007

(51) Int. Cl.
*G01N 33/18* (2006.01)
*G01D 11/24* (2006.01)

(52) U.S. Cl. ........................... 73/61.41; 73/431
(58) Field of Classification Search .............. 73/61.41, 73/431, 866.5
See application file for complete search history.

(56) References Cited

FOREIGN PATENT DOCUMENTS

JP           56-118614 A  *  9/1981  .................. 73/431

* cited by examiner

*Primary Examiner*—Daniel S Larkin
(74) *Attorney, Agent, or Firm*—Thomas R. Vigil

(57) ABSTRACT

A water quality detecting device for an aquarium includes a casing, a transparent cover and a seat. Two pairs of circular recesses are respectively defined in opposite ends of the upper and lower faces of the casing. A close water guiding groove is defined in the upper and lower faces and opposite side faces of the casing connecting the circular recesses. A positioning slot is defined in the center of the rear face of the casing close the bottom edge. The transparent cover includes a covering board, and upper and lower sidewalls extending perpendicularly from the upper and lower edges of the covering board and respectively covering the circular recesses and the water guiding groove. A pair of cylindrical posts is disposed at inner sides of the upper and lower sidewalls close one end thereof for correspondingly extending into one pair of circular recesses. The seat includes a flat board, a first insertion member upwardly and slantingly extending from the center of the flat board for extending into the positioning slot, and a second insertion member disposed behind the first insertion member for extending into the positioning slot in a reverse direction.

7 Claims, 7 Drawing Sheets

WATER QUALITY DETECTING DEVICE FOR AN AQUARIUM

FIELD OF THE INVENTION

The present invention relates to a water quality detecting device, an particularly to a water quality detecting device for an aquarium which can prevent in leakage of hydrosphere or liquid and can be suspended or flatwise fixed.

DESCRIPTION OF THE PRIOR ART

Since people pay more and more attention to living quality, besides daily necessities, people gradually pay more attention to fun of home living. An aquarium is often placed in the house for fun. As progress of biology technology, more and more types of aquatic organisms can be fed in the aquarium. Most of fish or aquatic animals and plants can beautify the environment and are enjoyable in seeing. Therefore, there is always a proper position to place an aquarium in a drawing room or a living room.

Since a lot of aquatic animals and plants are fed in aquariums, it is important to monitor and control water quality of the aquariums for providing good living conditions to the aquatic animals and plants thereby showing the best of the aquarium. Since the aquarium forms a closed circulation system, excretion from the aquatic animals and plants or micro-organisms and bacteria in water may cause water pollution in the aquarium due to slight carelessness, which may adversely affect the living of the aquatic animals and plants even make the aquatic animals and plants dead. Therefore, it is important to have a device for detecting water quality of the aquarium.

Referring to FIG. 1 showing a schematic view of a conventional water quality detecting device, the water quality detecting device 10 includes a body 11, a cover 14, a detecting signal line 12 and a power line 13. The detecting signal line 12 and the power line 13 extend from the top of the body 11 and are coupled to a detecting control module (not shown) disposed inside the body. The connector of the detecting signal line 12 is made of metal. Since the detecting device is readily affected by the hydrosphere or drip around the aquarium, the metal connector of the detecting line signal may rust, even the drip in leaks into the detecting device which results in damage of modules inside the body. In addition, the cover 14 only covers a display and operation panel disposed at the center of the detecting device. That is, the cover 14 does not cover the whole upper surface of the detecting device. Thus, drip may in leak into the display and operation panel from the top edge of the cover 14. Moreover, since the body of the water quality detecting device is directly fixed at the top of the aquarium, water may easily to flow into the detecting device and no other fixing manners can be selected by a user.

Accordingly, it is desired to improve the conventional water quality detecting device for an aquarium.

SUMMARY OF THE INVENTION

An object of the present invention is to provide a water quality detecting device for an aquarium which has a seat for suspending or flatwise fixing the water quality detecting device whereby the water quality detecting device may be alternately disposed.

Another object of the present invention is to provide a water quality detecting device for an aquarium which has a transparent cover and a casing for preventing water from in leakage into the water quality testing device.

A further object of the present invention is to provide a water quality detecting device for an aquarium having a transparent cover and a casing for selectively pivoting the cover at the left or right side of the casing.

Other objects, advantages and novel features of the present invention will be drawn from following detailed embodiment of the present invention with attached drawings; in which:

DETAILED DESCRIPTION OF THE INVENTION

Figure 1:
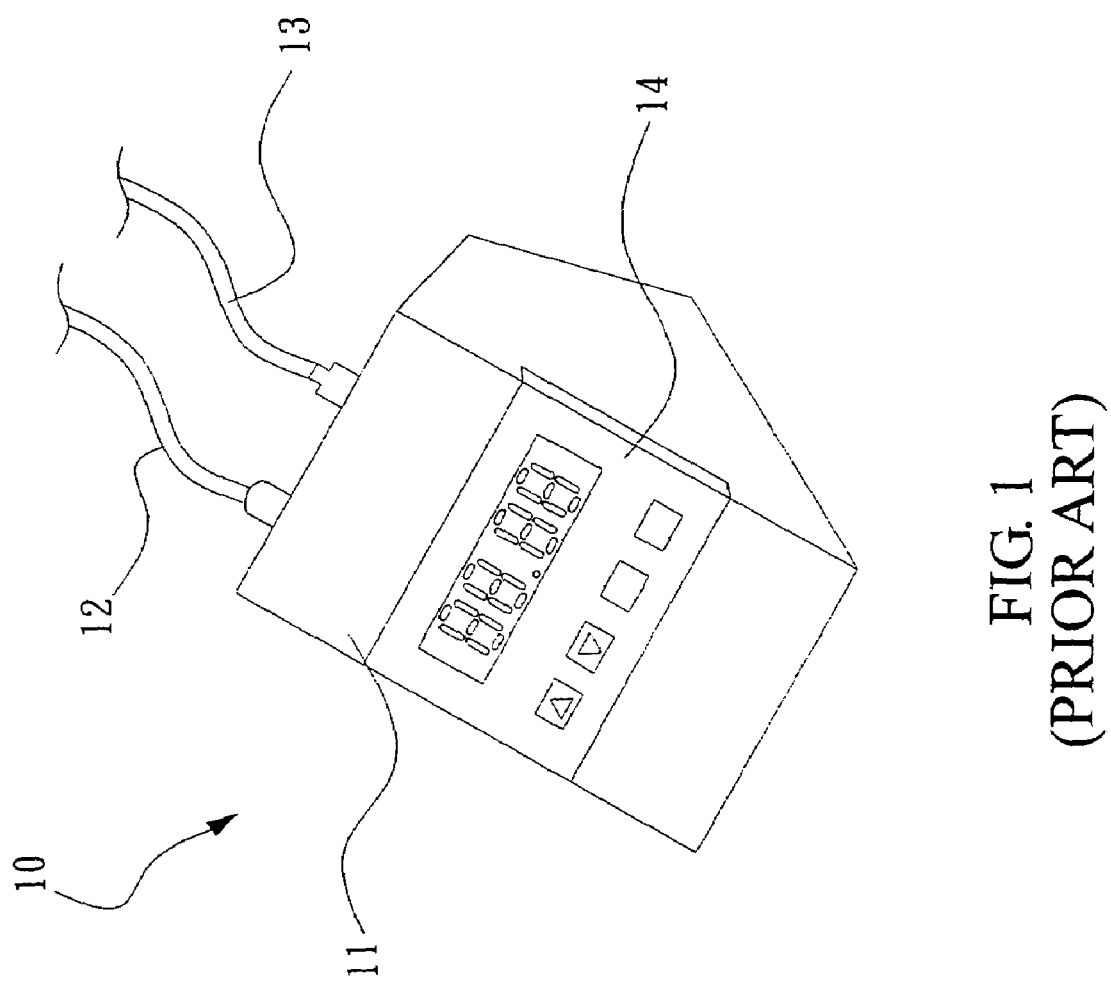
FIG. 1 is a perspective view of a conventional water quality detecting device.
Figure 2:
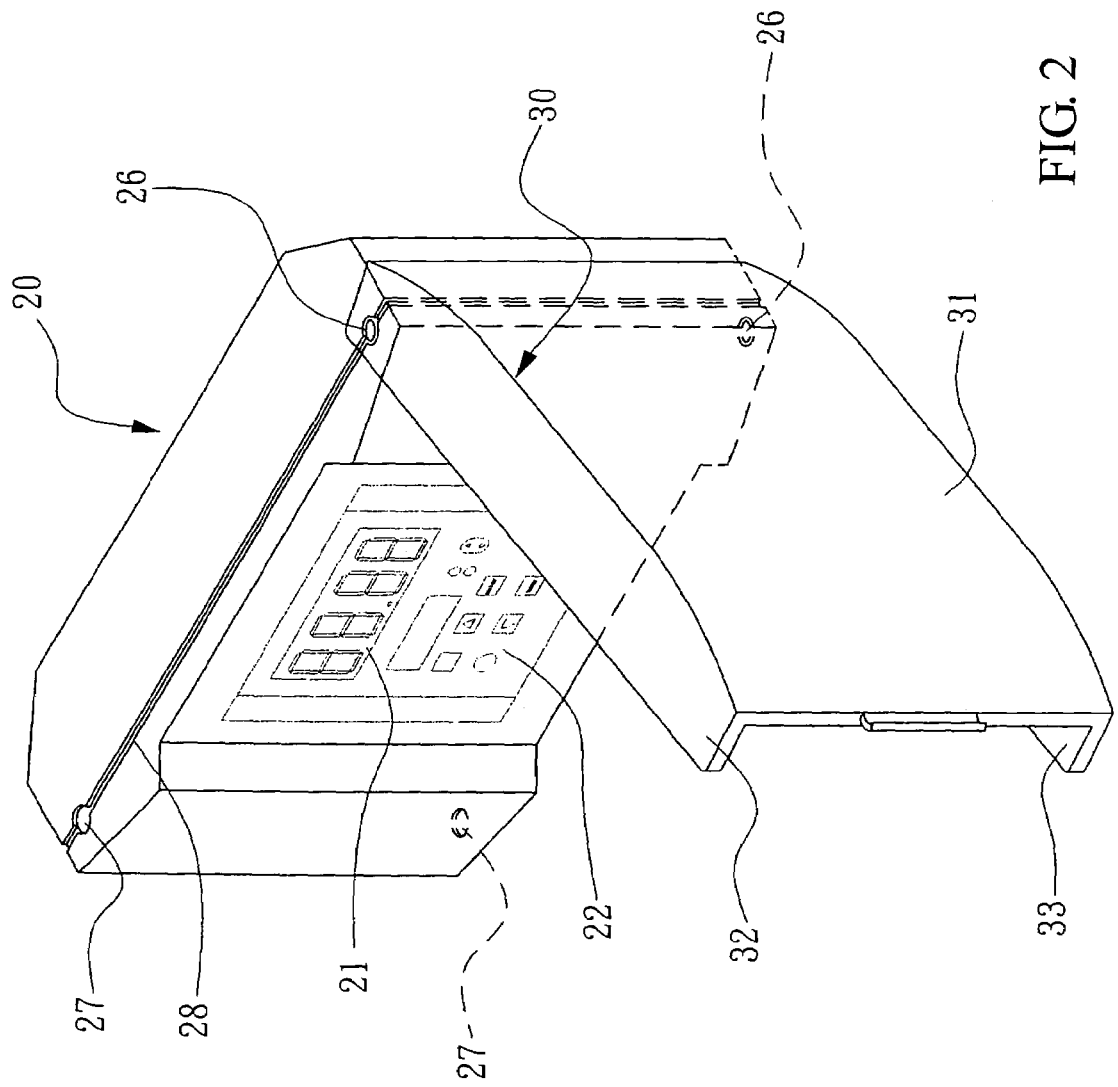
FIG. 2 is a perspective view of a casing and a cover.
Figure 3:
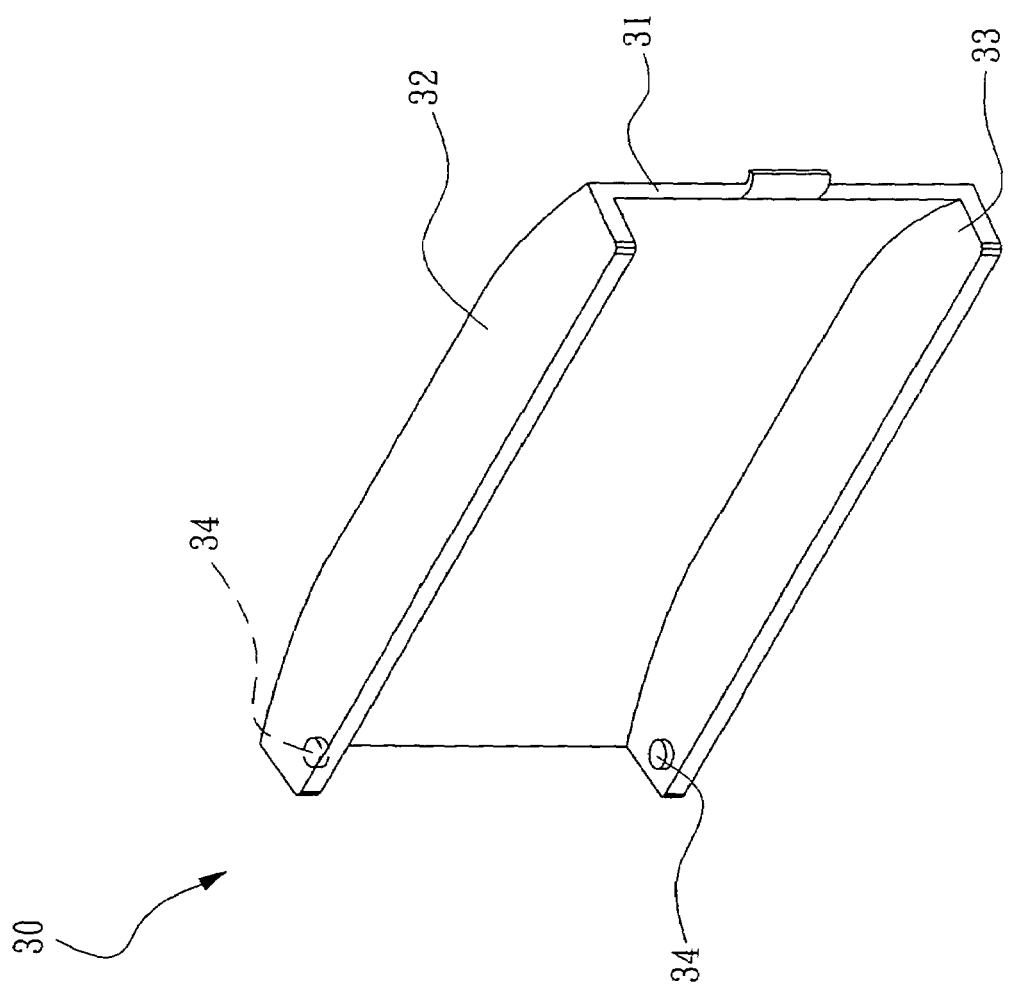
FIG. 3 is a perspective view if the cover of FIG. 2.
Figure 4:
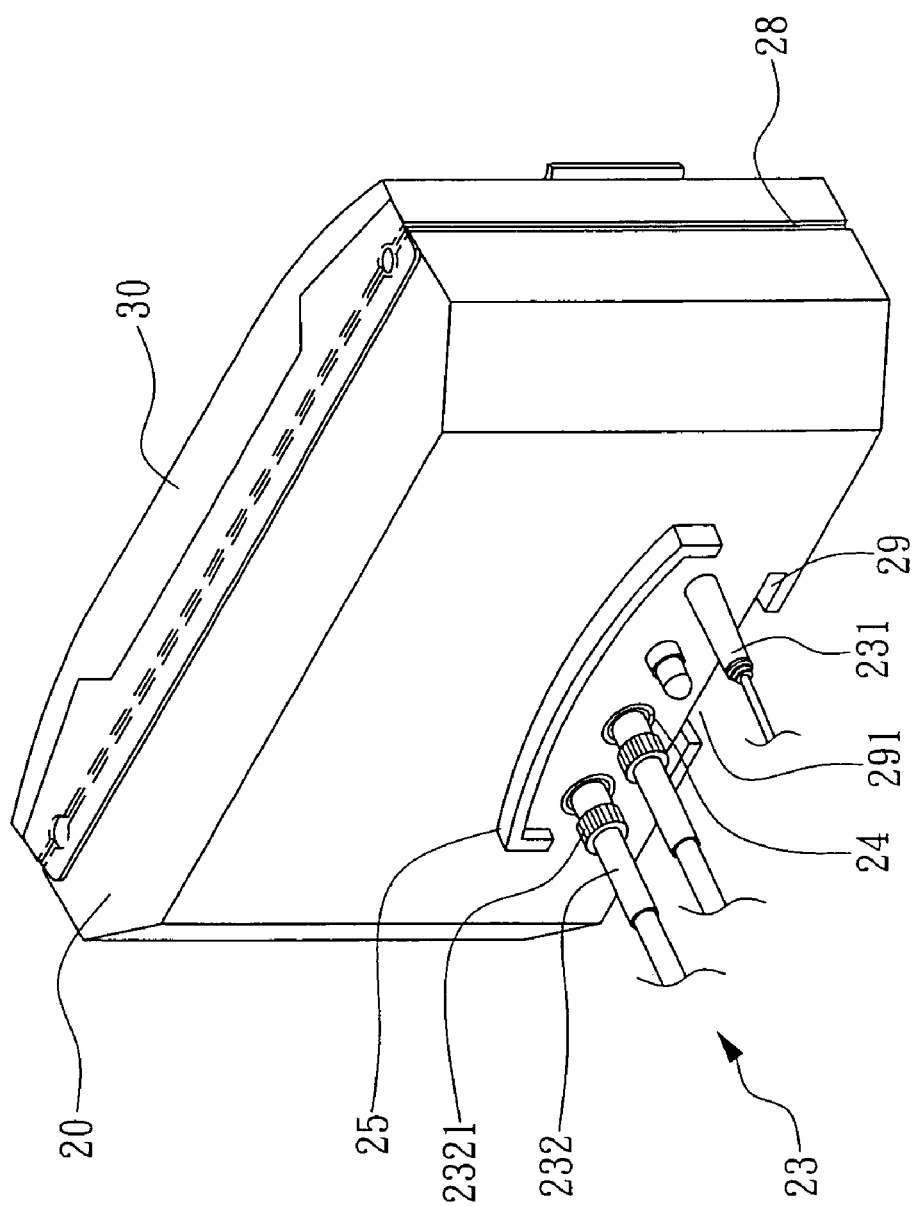
FIG. 4 is a perspective view showing a rear face of the casing.

Referring to FIGS. 2-5, the present invention discloses a water quality detecting device for an aquarium having a detecting module (not shown) for detecting water quality variation of an aquarium. The water quality detecting device includes a casing 20, a transparent cover 30 and a seat 40. The casing 20 is rectangular for receiving the detecting module. The casing 20 is disposed with a display 21 and an operation panel 22 coupled to the detecting module at the front face thereof and is defined with a plurality of through holes 24 at the rear face thereof for providing insertion or access of wires 23 coupled to the detecting module, as shown in FIG. 4. The wires 23 includes a power line 231, a detector connection wire 232 and so on. In addition, an arcuate baffle 25 extends perpendicularly and outwardly from the rear face of the casing 20 above the plurality of through holes 24.

In addition, referring to FIG. 2, two pairs of circular recesses 26, 27 are respectively defined in opposite ends of the upper and lower faces of the casing 20. A close water guiding groove 28 is defined in the upper and lower faces and opposite side faces of the casing 20 connecting the circular recesses 26, 27. As shown in FIG. 4, a positioning slot 29 is defined in the center of the rear face of the casing 20 close to the bottom edge. A cutout 291 is defined in the lower face of the casing 20. The cutout 291 is in communication with the positioning slot 29 and is smaller than the positioning slot 29 thereby cooperatively forming a T-shaped mounting slot.

As shown in FIG. 3, the transparent cover 30 includes a covering board 31 coverable the front face of the casing 20, and upper and lower sidewalls 32, 33 extending perpendicularly from the upper and lower edges of the covering board 31 and respectively covering the circular recesses 26, 27 and the water guiding groove 28 disposed at the upper and lower faces of the casing 20. A pair of cylindrical posts 34 is disposed at inner sides of the upper and lower sidewalls 32, 33 close one end thereof for correspondingly extending into the circular recesses 26 or 27. Therefore, when the cylindrical posts 34 of the transparent cover 30 are respectively received in the circular recesses 26 or 27 of the casing 20, the transparent cover 30 is rotatable about the pair of cylindrical posts 34.

Figure 5:
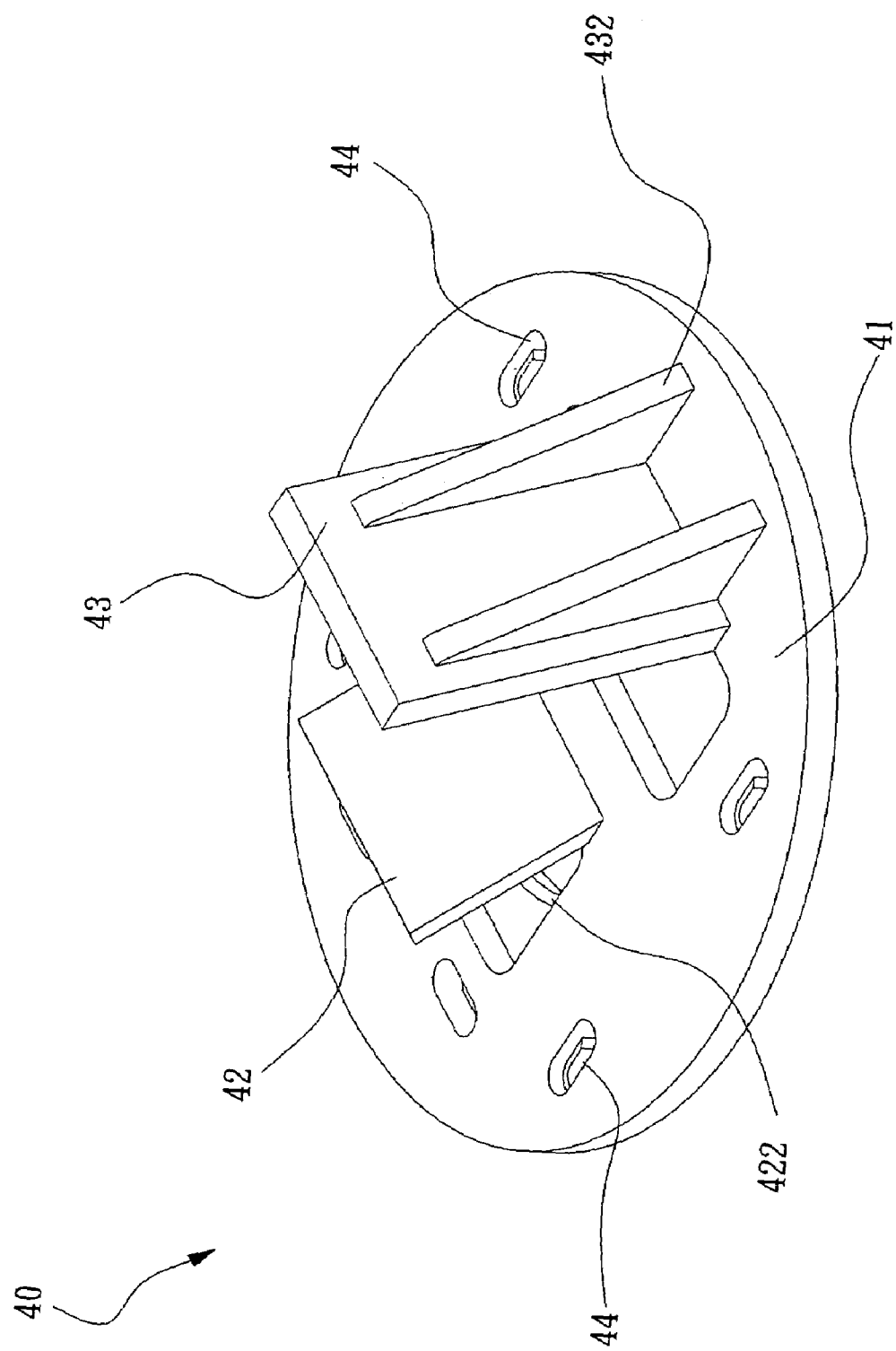
FIG. 5 is a perspective view of a seat of the present invention.

Referring to FIG. 5, the seat 40 includes a flat board 41, a first insertion member 42 upwardly and slantingly extending from the center of the flat board 41, for extending into the positioning slot 29, and a second insertion member 43 disposed behind the first insertion member 42 for extending into the positioning slot 29 in a reverse direction. The second insertion member 43 is longer in length than the first insertion member 42 and has a larger elevation angle than the first insertion member 42. A plurality of symmetrical protrusions 421, 431 is respectively formed at the first insertion member 42 and the second insertion member 43 for providing a mounting friction force between the first insertion member 42, or the second insertion member 43 and the positioning slot 29 of the casing 20.

A lateral support beam 422 is disposed between the first insertion member 42 and the flat board 41 for supporting the first insertion member 42. Two longitudinal enhancing ribs 432 extend from the second insertion member 43 away from the first insertion member 42, and connect to the flat board 41.

In addition, a plurality of fixing holes 44 is defined in the flat board 41 of the seat 40 for extension of a fixing module (not shown) thereby fixing the seat 40 to a wall.

Figure 6:
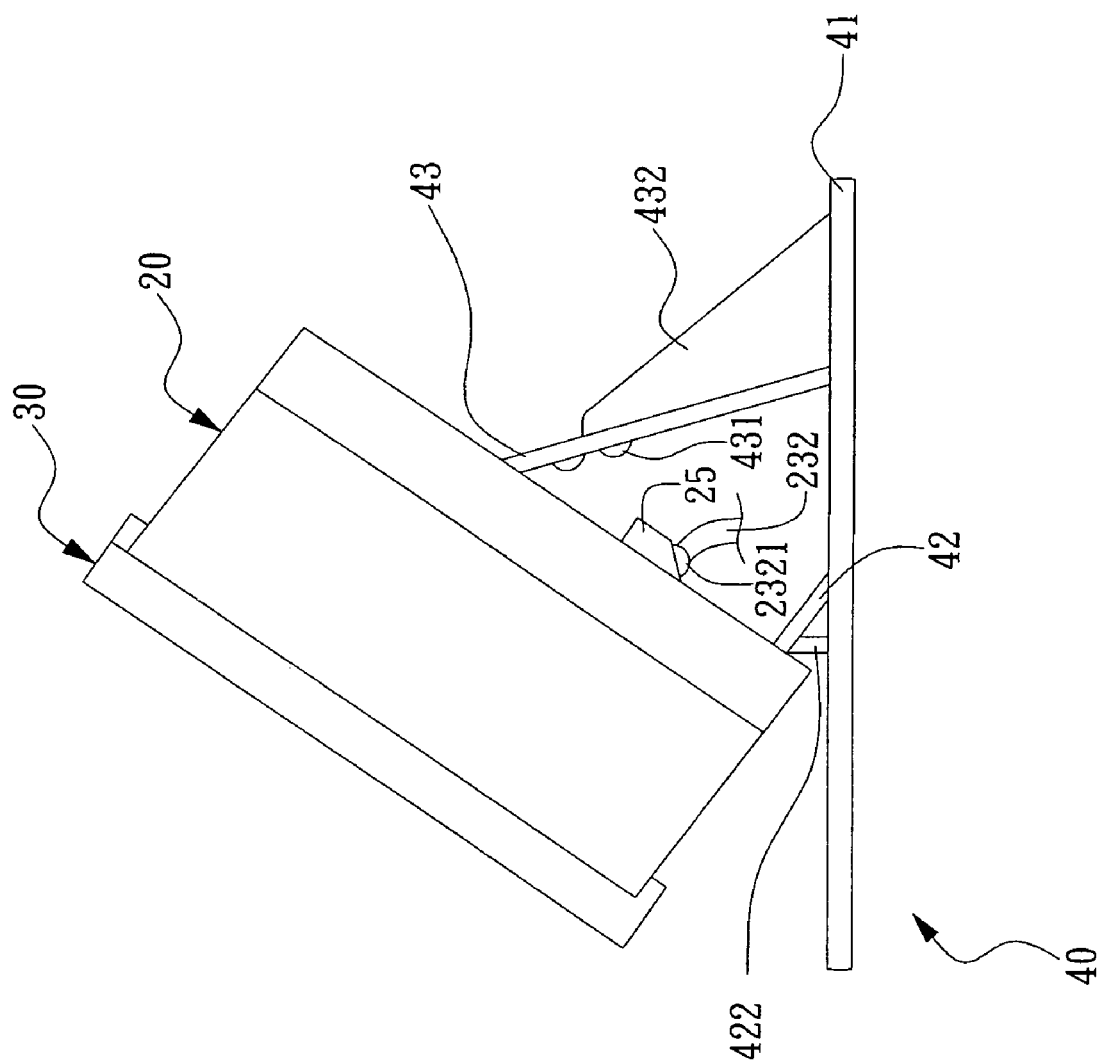
FIG. 6 is a schematic view showing the water quality detecting device of the present invention is flatwise fixed.
Figure 7:
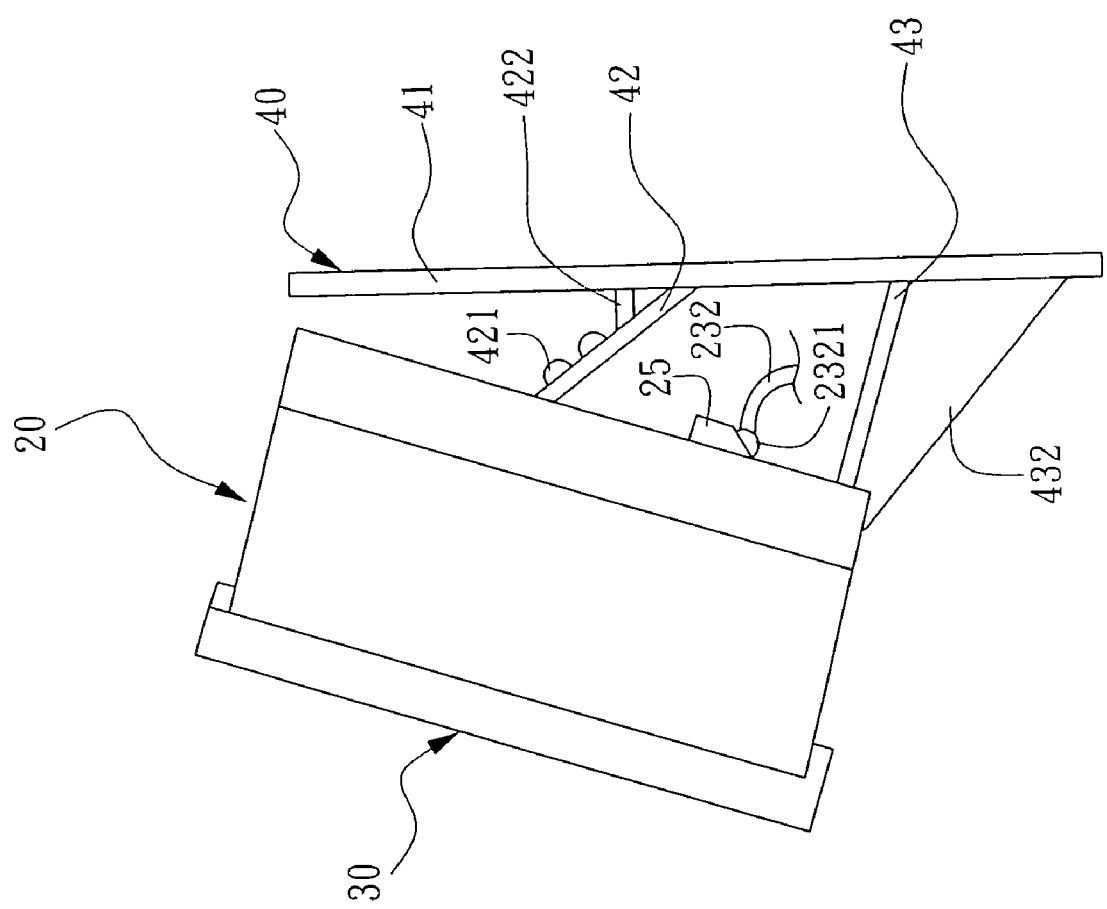
FIG. 7 is a schematic view showing the water quality detecting device of the present invention is suspended.

FIGS. 6 and 7 show the seat 40 connecting the casing 20. As shown in FIG. 6, the seat 40 is flatwise disposed at the top of an aquarium (not shown. The positioning slot 29 of the casing 20 receives the first insertion member 42 with the rear face of the casing 20 abutting against the top of the second insertion member 43, whereby the casing 20 is slantingly and flatwise disposed to the top of the aquarium. In addition, as shown in FIG. 7, the flat board 41 of the seat 40 is fixed to the wall, and the second insertion member 43 is disposed below the first insertion member 42. The positioning slot 29, of the casing 20 receives the second insertion member 43 and the rear face of the casing 20 abuts against the top of the first insertion member 42, whereby the casing 20 is slantingly suspended at the wall.

Referring to FIG. 2, when the pair of cylindrical posts 34 of the transparent cover 30 is received in one pair of circular recesses 26 of the casing 20, the transparent cover 30 is pivotable about the pair of circular recesses 26 and is so opened from the left side of the casing 20 toward the right side of the casing 20. In addition, when the cover 30 is reversed and the pair of cylindrical posts 34 is received in the circular recesses 27 of the casing 20, the transparent cover 30 is pivotable about the pair of circular recesses 27 and so is opened from the right side of the casing 20 toward the left side of the casing 20.

Since the transparent cover 30 fully covers the display 21 and the operation panel 22 of the casing 20 and the water guiding groove 28 of the casing 20 can block water from flowing into the front face of the casing 20, the present invention can fully prevent water from in leakage into the casing 20.

In addition, as shown in FIGS. 6-7, in use of the water quality detecting device of the present invention, the casing 20 is slantingly disposed with the front face facing upwardly. Therefore, even though some water slides on the rear face of the casing 20, the water may be blocked by the arcuate baffle 25 disposed on the rear face of the casing 20 for preventing water from directly dripping at the metal connector 2321 of the detector connection wire 232 thereby preventing the metal connector 2321 from rusting.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A water quality detecting device for an aquarium having a detecting module for detecting water quality of the aquarium, the water quality detecting device comprising:
   a casing which is rectangular for receiving the detecting module, the casing being disposed with a display and an operation panel coupled to the detecting module at the front face thereof and being defined with a plurality of through holes at the rear face thereof for providing insertion or access of wires coupled to the detecting module, an arcuate baffle extending perpendicularly and outwardly from the rear face of the casing above the plurality of through holes, two pairs of circular recesses being respectively defined in opposite ends of the upper and lower faces of the casing, a close water guiding groove being defined in the upper and lower faces and opposite side faces of the casing connecting the circular recesses, a positioning slot being defined in the center of the rear face of the casing close the bottom edge;
   a transparent cover comprising a covering board covering the front face of the casing, and upper and lower sidewalls extending perpendicularly from upper and lower edges of the covering board and respectively covering the circular recesses and the water guiding groove disposed at the upper and lower faces of the casing, a pair of cylindrical posts being disposed at inner sides of the upper and lower sidewalls close one end thereof for correspondingly extending into one pair of circular recesses; and
   a seat comprising a flat board, a first insertion member upwardly and slantingly extending from the center of the flat board for extending into the positioning slot, and a second insertion member disposed behind the first insertion member for extending into the positioning slot in a reverse direction, the second insertion member being longer in length than the first insertion member and having a larger elevation angle than the first insertion member.

2. The water quality detecting device of claim 1, wherein a plurality of symmetrical protrusions is formed on the first insertion member for providing a mounting friction force between the first insertion member and the positioning slot of the casing.

3. The water quality detecting device of claim 1, wherein a plurality of symmetrical protrusions is formed on the second insertion member for providing a mounting friction force between the second insertion member and the positioning slot of the casing.

4. The water quality detecting device of claim 1, wherein a plurality of fixing holes is defined in the flat board of the seat for extension of a fixing module.

5. The water quality detecting device of claim 1, wherein a lateral support beam is disposed between the first insertion member and the flat board for supporting the first insertion member.

6. The water quality detecting device of claim 1, wherein at least one longitudinal enhancing rib extends from the second insertion member away from the first insertion member, and connects to the flat board.

7. The water quality detecting device of claim 1, wherein a cutout is defined in the lower face of the casing, and the cutout is in communication with the positioning slot and is smaller than the positioning slot thereby cooperatively forming a T-shaped mounting slot.

* * * * *